United States Patent [19]
Willi

[11] Patent Number: 5,658,346
[45] Date of Patent: Aug. 19, 1997

[54] INNER SHELL FOR AN ARTIFICIAL HIP JOINT SOCKET

[75] Inventor: Roland Willi, Neftenbach, Switzerland

[73] Assignee: Sulzer Medizinaltechnik AG, Winterthur, Switzerland

[21] Appl. No.: 537,061

[22] Filed: Sep. 29, 1995

[30]    Foreign Application Priority Data

Nov. 30, 1994  [EP]  European Pat. Off. ............. 94810677

[51] Int. Cl.⁶ .................................................. A61F 2/32
[52] U.S. Cl. ................................. 623/22; 623/18
[58] Field of Search ........................ 623/16, 18, 19, 623/21, 22, 23

[56]                References Cited

U.S. PATENT DOCUMENTS 3,818,512  6/1974  Shersher ................................. 623/22
4,878,918  11/1989  Tari et al. .............................. 623/22

FOREIGN PATENT DOCUMENTS 0313773   5/1989  European Pat. Off. ............... 623/22
0 445 068  9/1991  European Pat. Off. .
0 586 335  3/1994  European Pat. Off. .
0 610 146  8/1994  European Pat. Off. .
3446048  10/1985  Germany .............................. 623/22

Primary Examiner—David Isabella
Attorney, Agent, or Firm—Townsend and Townsend and Crew LLP

[57]                 ABSTRACT

An inner shell for insertion into an outer shell to thereby form a hip joint socket. The inner shell includes an outwardly projecting thread spigot located at a pole with the thread spigot defining a rotational axis and being screwable into an inner thread of the outer shell. The inner shell further includes a projection arranged at the outer edge and extends outwardly radially to the rotational axis. The projection includes at least one locking part that acts on the outer shell, when the inner shell is placed within the outer shell, in order to prevent rotation of the inner shell about the rotational axis.

13 Claims, 2 Drawing Sheets

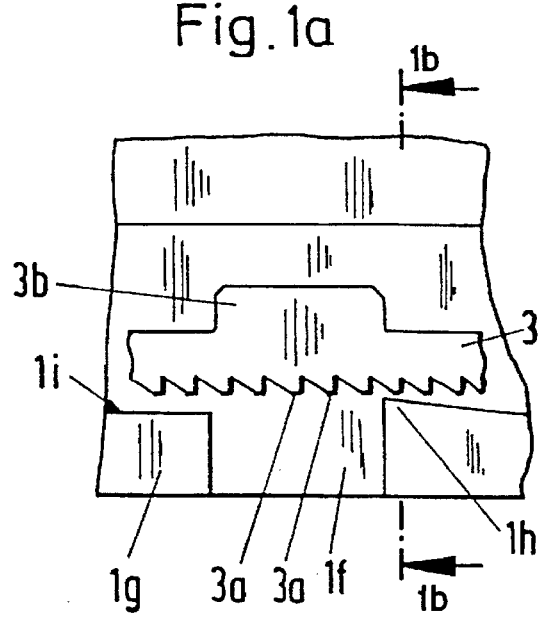
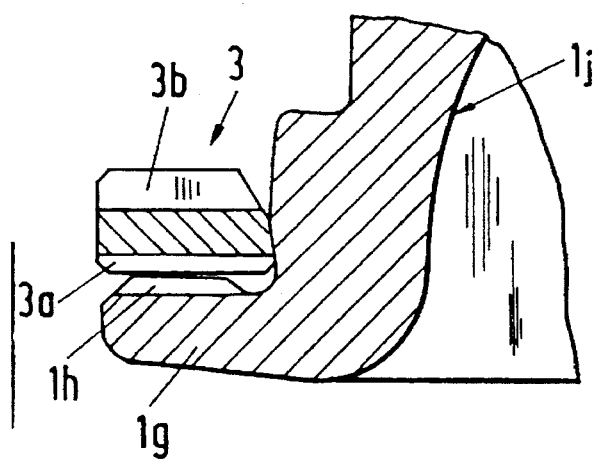
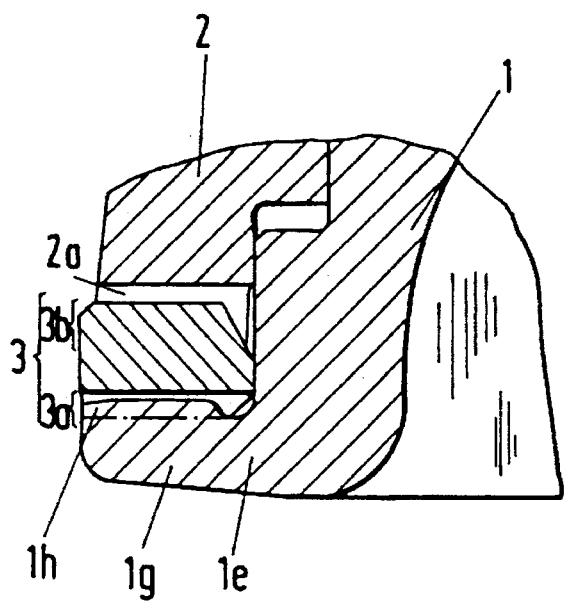
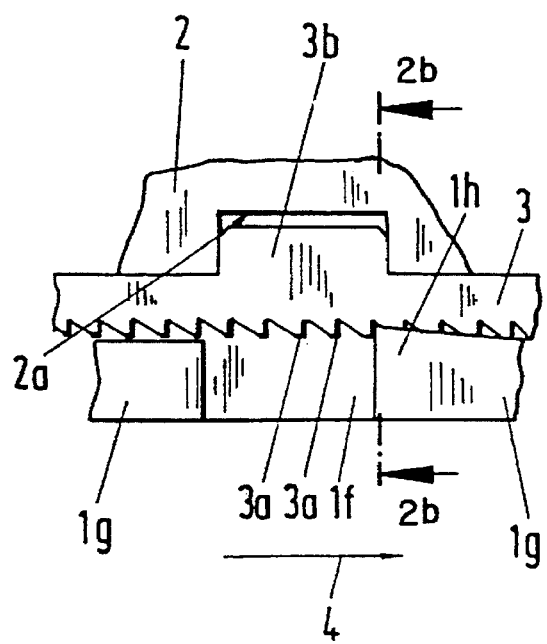

INNER SHELL FOR AN ARTIFICIAL HIP JOINT SOCKET

BACKGROUND OF THE INVENTION

1. Technical Field

The invention relates to an inner shell for an artificial hip joint socket and, more particularly, to a hip joint socket having an inner shell and to a method which allows the inner shell to be combined with a known outer shell to form a hip joint socket.

2. Description of the Prior Art

Artificial hip joint sockets (Acetabulae) often have a two-part construction comprising an anchorage body or outer shell to be fixed in the bone and a socket body or inner shell for the receipt of an articular head.

A two-part hip joint socket is, for example, known from EP 0 313 762 A1 comprised an anchorage body in the form of a hemispherical shell which can be fixed in the pelvis with the aid of bone screws as well as a socket body with a socket shell in which the articular head is seated. The socket body, which is made of plastic, is fixable in the anchorage body by a snap connection. Plastic socket bodies have the disadvantage that the socket shell wears down as a result of the long-term action of the articular head so that during a reoperation, the replacement of the worn socket head or of the entire hip joint socket can be necessary.

SUMMARY OF THE INVENTION

The object of the invention is to provide an inner shell with reduced wear properties which can be fitted in an existing anchorage body of the type originally designed for the receipt of a plastic inner shell.

An inner shell in accordance with the present invention is made of metal and has a threaded spigot at its pole which projects outwardly, defines a rotational axis, and which can be screwed into an inner thread of an outer shell. An inner shell of this kind has the advantage that, during a reoperation, a plastic socket body can be replaced by the inner shell of the invention by inserting the inner shell into the existing anchorage body fixed in the bone. The projecting thread spigot is screwed into the inner thread of the outer shell so that the inner shell is held in the outer shell via this connection element. The inner shell further comprises a projection arranged at the outer edge extending outwardly radial to the rotational axis. This projection includes at least one locking part which, when the inner shell is installed in the outer shell, acts on the outer shell directly or via an additional intermediate part in order to prevent a rotation of the inner shell about its rotational axis. It is thus ensured that the inner shell cannot work loose from the outer shell. Moreover, there is a mutual mechanical connection in the region of the opening of inner shell and outer shell so that the inner shell is fixedly held in the outer shell.

A further advantage of the invention is that the inner shell can be secured to numerous different outer shell embodiments, in particular also to outer shells which are fixed or which can be fixed to the pelvis bone in different ways. For example, these can be outer shells fixed with bone screws or threads arranged on the outer surface or securing methods characterized by press fittings or snap fittings.

BRIEF DESCRIPTION OF THE DRAWINGS

FIG. 1a is a side elevation view of a portion of a metallic inner shell in accordance with the present invention;

FIG. 1b is a sectional view of the inner shell of the invention along the line 1b—1b of FIG. 1a;

FIG. 2a is a side elevation view of an artificial hip joint socket comprising an inner shell and an outer shell;

FIG. 2b is a sectional view of the artificial hip joint socket along the line B—B of FIG. 2a;

DETAILED DESCRIPTION OF THE PREFERRED EXEMPLARY EMBODIMENTS

Figure 4:
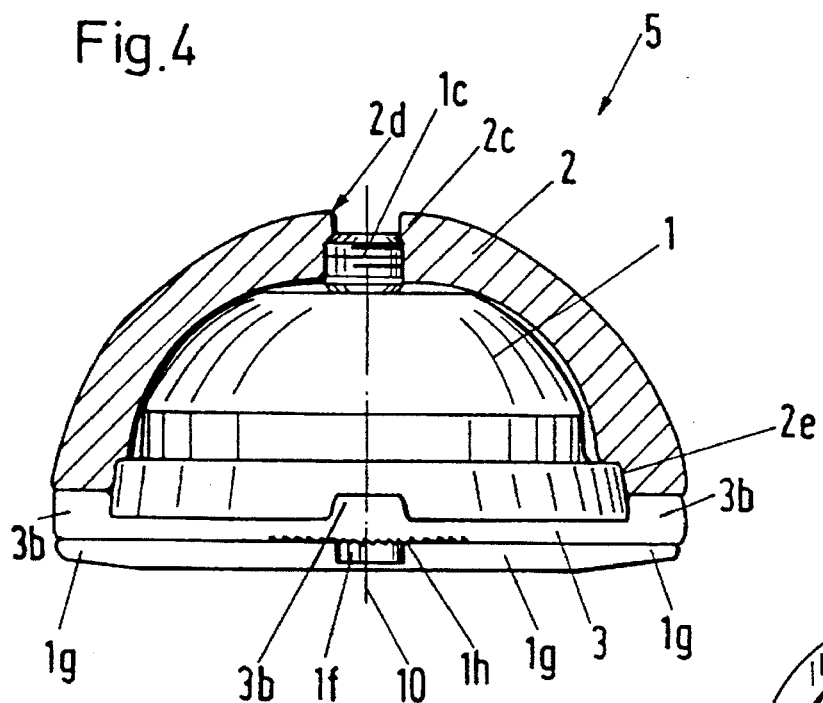
FIG. 4 is a side elevation view of a hip joint socket with a partial sectional view of the outer shell.

FIG. 4 shows an assembled hip joint socket 5 having a metallic inner shell 1, a securing ring 3, as well as an outer shell 2 sectioned along a meridian for the sake of better illustration. The outer shell 2 has a pole 2c at which a cylinder-shaped perforation or through-hole with an inner thread 2d is arranged. The outer shell 2 further comprises an opening 2e. The outer shell 2 is anchored as well as possible in the pelvis bone. Different kinds of anchoring methods are known for anchoring an outer shell 2 in the pelvis bone: for example by means of bone screws; by means of a thread arranged on the outer surface of the outer shell 2; by means of cementing the outer shell into the pelvis bone or via press or snap fit connections.

Figure 3:
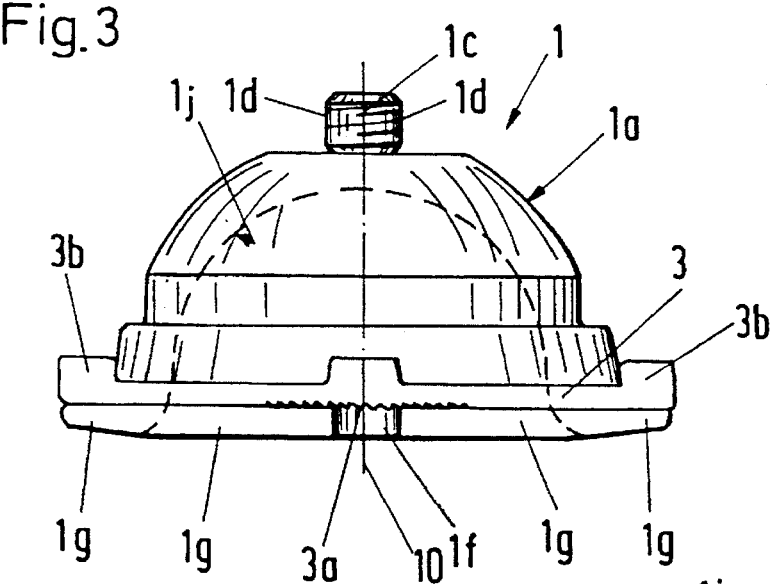
FIG. 3 is a side elevation view of a metallic inner shell with a securing ring.
Figure 6:
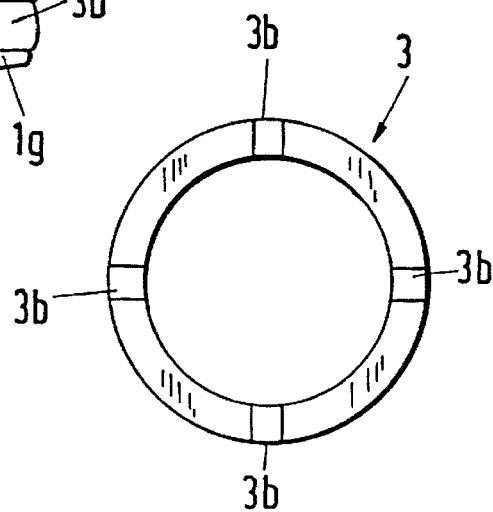
FIG. 6 plan is a view onto a securing ring.

FIG. 3 illustrates an inner shell. The inner shell 1 has an outer surface 1a as well as an inner volume 1j which serve to receive the articular head or joint head. The pole of the inner shell has a cylinder-shaped pole part 1c which defines an axial direction 10 and which has an outer thread 1d. In the region of the opening of the inner shell 1, which is normally arranged in the equatorial region of the inner volume 1b, the inner shell 1 has a projection 1g arranged at the outer edge of the inner shell 1 and extending outwardly radial to the rotational axis 10. The projection 1e can extend closed around the outer edge of the inner shell 1 or may also have perforations 1f. The projection 1g has a circular ring-shaped surface 1i on the side facing towards the thread spigot 1c, wherein the surface can be partly interrupted by perforations 1f. A securing ring 3 lies on this circular ring-shaped surface 1i and, as illustrated in FIG. 6, is constructed with a circular shape with coupling parts 3b spaced at regular intervals directed towards the pole of the inner shell 1. The securing ring 3 has a sawtooth-shaped surface structure 3a on its side facing away from the pole of the inner shell as illustrated in FIG. 3.

Figure 5:
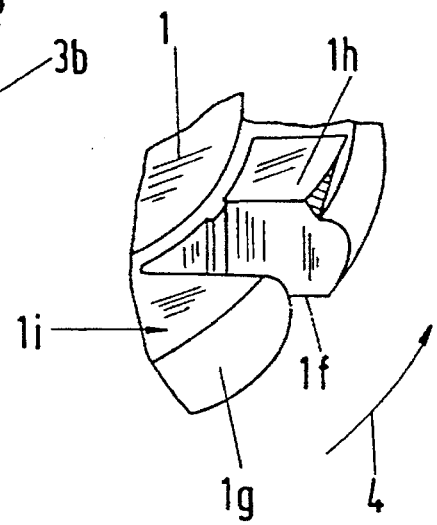
FIG. 5 is an enlarged perspective view of portion of an inner shell having a locking part.

FIG. 5 shows in a detailed view of the inner shell 1 a projection 1g of the inner shell having a perforation 1f as well as the circular ring-shaped surface 1i. On the circular ring-shaped surface 1i, a projecting part 1h is arranged which serves as a locking part 1h. The direction of rotation 4 of the inner shell on screwing in the inner shell 1 into the outer shell 2 is also illustrated, wherein, during this process, the inner shell 1 rotates about the axial direction 10.

FIG. 1a illustrates a side view of the inner shell 1 in a detailed view. The side view shows the projection 1g, a recess 1f, the circular ring-shaped surface 1i, as well as the projecting part 1h. The securing ring 3, with the coupling part 3b and sawtooth-shaped part 3a, is also shown. FIG. 1b illustrates a section along the line 1b—1b of FIG. 1a. The inner volume 1j as well as the projection 1g with locking part 1h arranged at the outer edge are visible from the inner shell 1. Moreover, the intermediate part formed as the securing ring 3 is illustrated with the coupling part 3b and the sawtooth-shaped part 3a. The profile of the teeth in the sawtooth-shaped part 3a and the profile of the projecting part 1h are matched to one another so that a mutual rotation between the securing ring 3 and the inner shell 1 is prevented as soon as the sawtoothed part 3a is engaged with the locking part 1b. In the present embodiment, the part 3a is illustrated having a sawtooth shape and the locking part 1h as a projecting part. There is naturally a plurality of possibilities for the embodiments of these two parts in order to effect the prevention of mutual rotation, so that the embodiment illustrated is only to be viewed as one of a plurality of possible embodiments.

FIG. 2a shows a section from a side view of a hip joint socket 5 comprising an inner shell 1 with projection 1g, perforation 1f, and locking part 1h, as well as an outer shell 2 with recess 2a and an intermediate piece or securing ring 3 with coupling part 3b and sawtoothed part 3a. In the arrangement illustrated, the inner shell is screwed into the outer shell 2 and thereby fixed, wherein the coupling part 3b engages into a recess or groove 2a of the outer shell 2, and wherein the sawtooth-shaped part 3a has undergone a plastic deformation in the region of the projecting part 1h so that the inner shell 1 and the outer shell 1 are secured against a mutual relative movement in the direction of rotation 4 so that the inner shell and the outer shell are reliably and securely connected to one another. FIG. 2b illustrates a section along the line B—B of FIG. 2a. The inner shell 1 is once more visible with the projection 1g arranged at the outer edge 1e as well as the outer shell 2. Also visible is the position of the securing ring 3 which, in the upper part as the coupling part 3b, engages into the recess 2a of the outer shell 2 and which, in the lower part as the sawtooth-shaped part 3a, is in engagement with the locking part or projecting part 1h. The connection illustrated acts as a safety against rotation between the inner shell 1 and the outer shell 2 and, moreover, effects a support of the inner shell 1 on the outer shell 2. The intermediate part 3 can be made of plastic or metal, wherein the metal needs to have a certain softness or elasticity in order to be deformable to a certain extent.

A further embodiment (not shown) can be designed in such a manner that the inner shell 1 and the outer shell 2 are connected to one another in a manner secured against rotation without an intermediate part 3 by providing that a correspondingly designed locking part 1h directly exerts an engaging connection to a recess 2a in the outer shell 2 and thereby prevents a mutual rotation between the inner shell 1 and outer shell 2.

The inner shell 1 and outer shell 2 are put together in such a manner that the thread spigot 1c of the inner shell is screwed into an inner thread 2d of the outer shell and the inner shell is screwed in up to the point at which an engaging connection between the locking part 1h and the outer shell 2 is achieved so that the inner and outer shells are connected to one another in a manner secured against rotation. An intermediate piece 3, such as a ring-shaped intermediate piece, can, for example, also be used which is arranged between outer shell 2 and inner shell 1 in such a manner that it plastically deforms during the screwing together and thereby prevents a mutual rotation of outer shell 2 and inner shell 1.

What is claimed is:

1. An inner shell for insertion into an outer shell to thereby form a hip joint socket, the inner shell including an outwardly projecting thread spigot located at a pole, the thread spigot defining a rotational axis and being screwable into an inner thread of the outer shell, and the inner shell further including a projection arranged at an outer edge opposite said pole and extending outwardly and radially to the rotational axis, wherein the projection includes at least one locking part that acts on the outer shell, when the inner shell is placed within the outer shell, in order to prevent rotation of the inner shell about the rotational axis.

2. An inner shell in accordance with claim 1 wherein the inner shell is metallic.

3. An inner shell in accordance with claim 1, wherein the locking part acts on the outer shell directly in order to prevent rotation of the inner shell about the rotational axis.

4. An inner shell in accordance with claim 1 wherein the locking part acts on the outer shell via an intermediate piece in order to prevent rotation of the inner shell about the rotational axis.

5. An inner shell in accordance with claim 1 wherein the projection has a circular ring-shaped surface on a surface facing towards the thread spigot, and wherein the locking part projects out of the circular ring-shaped surface in a direction towards the thread spigot.

6. An inner shell in accordance with claim 5 wherein the locking part has a sawtooth shape.

7. An inner shell in accordance with claim 5 wherein the ring-shaped surface has perforations and the locking part is arranged adjacent to a perforation.

8. A hip joint socket comprising an outer shell and an inner shell, the inner shell including an outwardly projecting thread spigot located at a pole, the thread spigot defining a rotational axis and being screwable into an inner thread of the outer shell, the inner shell further including a projection arranged at an outer edge opposite said pole and extending outwardly and radially to the rotational axis, the projection including at least one locking part that acts on the outer shell, when the inner shell is placed within the outer shell, in order to prevent rotation of the inner shell about the rotational axis, and wherein an intermediate part is formed as a ring-shaped element lying on a surface of the inner shell and has at least one part projecting towards the thread spigot, the one part engaging a recess defined within the outer shell.

9. A hip socket in accordance with claim 8 wherein the inner shells and outer shells are metallic.

10. A hip socket in accordance with claim 8 wherein the intermediate piece is metallic.

11. A hip socket in accordance with claim 8 wherein the intermediate piece is plastic.

12. A hip socket in accordance with claim 8 wherein the intermediate part has a sawtooth shape defined on a surface facing the surface of the inner shell.

13. A method for connecting an outer shell with an inner shell, the inner shell including an outwardly projecting thread spigot located at a pole, the thread spigot defining a rotational axis, the inner shell further including a projection arranged at an outer edge opposite said pole and extending outwardly and radially to the rotational axis, the projection including at least one locking part that acts on the outer shell when the inner shell is placed within the outer shell, the method comprising the steps of:

laying a ring-shaped intermediate part on the projection of the inner shell;

screwing the thread spigot of the inner shell into an inner thread of the outer shell; and pressing the intermediate part between the outer shell and the projection of the inner shell such that the inner shell is held in the outer shell in a manner fixed against rotation about the rotational axis.

* * * * *